(12) United States Patent
Brocia

(10) Patent No.: US 11,879,115 B2
(45) Date of Patent: Jan. 23, 2024

(54) METHODS TO IMPROVE BEVERAGE QUALITY

(71) Applicant: Roar Holding LLC, New York, NY (US)

(72) Inventor: Robert W. Brocia, Bronxville, NY (US)

(73) Assignee: Roar Holding LLC, New York, NY (US)

( * ) Notice: Subject to any disclaimer, the term of this patent is extended or adjusted under 35 U.S.C. 154(b) by 758 days.

(21) Appl. No.: 16/696,898

(22) Filed: Nov. 26, 2019

(65) Prior Publication Data

US 2020/0165552 A1 May 28, 2020

Related U.S. Application Data

(60) Provisional application No. 62/917,188, filed on Nov. 26, 2018.

(51) Int. Cl.
| | | |
|---|---|---|
| *C12H 3/02* | (2019.01) | |
| *A61K 9/00* | (2006.01) | |
| *A61K 47/22* | (2006.01) | |
| *A61K 38/44* | (2006.01) | |
| *A61K 47/18* | (2017.01) | |

(52) U.S. Cl.
CPC ............ *C12H 3/02* (2019.02); *A61K 9/0095* (2013.01); *A61K 38/44* (2013.01); *A61K 47/18* (2013.01); *A61K 47/22* (2013.01); *C12Y 104/03004* (2013.01)

(58) Field of Classification Search
CPC . C12H 3/02; C12H 3/04; A61K 47/18; A61K 9/0095; A61K 47/22; C12G 3/08
See application file for complete search history.

(56) References Cited

U.S. PATENT DOCUMENTS

| | | | |
|---|---|---|---|
| 4,612,196 A | 9/1986 | Goldstein et al. | |
| 4,933,198 A | 6/1990 | Lee et al. | |
| 4,990,350 A | 2/1991 | Rohmann | |
| 5,811,456 A * | 9/1998 | Seman | C07C 281/04 |
| | | | 560/29 |
| 8,227,508 B2 | 7/2012 | Fowler et al. | |
| 8,409,834 B2 | 4/2013 | Burlew et al. | |
| 10,195,163 B2 | 2/2019 | Brocia | |

(Continued)

FOREIGN PATENT DOCUMENTS

| | | |
|---|---|---|
| EP | 0 531 155 | 3/1993 |
| RU | 97116168 | 8/1999 |

(Continued)

OTHER PUBLICATIONS

C. Theron (The use of Spinning Cone Column ("Dunlaag vakuumdistillasie") to reduce alcohol in wines, Jan. 1, 2006, as presented on the website of Wineland: https://www.wineland.co.za/the-use-of-spinning-cone-column-dun 1 aag-vaku u md isti llasie-to-reduce-alcohol-i n-wi nes/).

(Continued)

*Primary Examiner* — Vera Stulii
(74) *Attorney, Agent, or Firm* — MORRISON & FOERSTER LLP

(57) ABSTRACT

Agave derived beverages with improved quality contain enhanced ratios of MAO B to MAO A inhibitors or enhanced concentration of inhibitor of MAO B.

5 Claims, 5 Drawing Sheets

(56) References Cited

U.S. PATENT DOCUMENTS

| | | | |
|---|---|---|---|
| 10,842,841 B2 | 11/2020 | Brocia | |
| 11,160,774 B2 | 10/2021 | Brocia | |
| 2005/0245612 A1* | 11/2005 | Blass | A61K 33/06 514/649 |
| 2010/0178411 A1 | 7/2010 | Mayer | |
| 2011/0067123 A1 | 3/2011 | Andersen | |
| 2013/0334115 A1 | 12/2013 | Volker | |
| 2014/0106014 A1 | 4/2014 | Giuliano et al. | |
| 2015/0093470 A1 | 4/2015 | Hobson | |
| 2015/0136515 A1 | 9/2015 | Nowka et al. | |
| 2015/0290595 A1 | 10/2015 | Reddy | |
| 2015/0352173 A1 | 12/2015 | Madhavamenon et al. | |
| 2016/0074343 A1 | 3/2016 | Brocia | |
| 2018/0296629 A1 | 10/2018 | Brocia | |
| 2022/0047531 A1 | 2/2022 | Brocia | |

FOREIGN PATENT DOCUMENTS

| | | |
|---|---|---|
| WO | WO 1997/004072 | 2/1997 |
| WO | WO 2009/121155 | 10/2009 |
| WO | WO-2012/128534 | 9/2012 |
| WO | WO-2014/015417 | 1/2014 |
| WO | WO2016044473 A1 | 3/2016 |
| WO | WO-2018/187628 | 10/2018 |

OTHER PUBLICATIONS

Flockhart, "Dietary restrictions and drug interactions with monoamine oxidase inhibitors: an update," J Clin Psychiatry (2012) 73(suppl 1):17-24.

Skaliotis, "Beverage Applications using Spinning Cone Technology," Food Marketing & Technology (2012) Retrieved from the Internet: http://www.harnisch.com/uploads/tx-harnisch/food-03-12-26-28.pdf.

Spinning cone column as disclosed by Wikipedia (https;//Wikipedia.org/wiki/Spinnng-cone, pp. 1-3, year 2022). (Year: 2022).

Bandaruk et al., "Cellular uptake of quercetin and luteolin and their effects on monoamine oxidase-A in human neuroblastoma SH-SY5Y cells," Toxicology Reports (2014) 1:639-649.

Bolasco et al., "Focusing on New Monoamine Oxidase Inhibitors," Expert Opin Ther (2010) 20(7):909-939.

Crichton et al., "Zinc: Lewis Acid and Gene Regulator," Biological Inorganic Chemistry (Second Edition) (2012):229-246.

May et al., "Monoamine oxidase (MAO; E.C. 1.4.3.4) characteristics of platelets influenced by in vitro and in vivo ethanol on alcoholics and on control subjects," J Neural Transm Suppl (1994) 41:69-73.

Zakhari et al., "Alcohol Metabolism and Epigenetics Changes," Alcohol Research (2013) 35(1):6-16.

* cited by examiner

| Position | Tequila Name | Likes | Price |
|---|---|---|---|
| 1 | Don Julio 1942 | 290 | $109.99 |
| 2 | Fortaleza Reposado | 195 | $50 |
| 3 | Fortaleza Blanco | 176 | $41.99 |
| 4 | Casa Noble Añejo (2 yr) | 169 | $55 |
| 5 | Don Julio Añejo | 141 | $55.99 |
| 6 | Clase Azul Reposado | 132 | $79.99 |
| 7 | Fortaleza Añejo | 123 | NA |
| 8 | Don Julio Reposado | 113 | $49.99 |
| 9 | Don Julio Blanco | 106 | $49.99 |
| 10 | Casa Noble Reposado | 104 | $46.99 |
| 11 | Patron Silver | 94 | $42.99 |
| 12 | Casamigos Tequila Reposado | 84 | $42.99 |
| 12 | Jose Cuervo Reserva de la Familia | 84 | $99.99 |
| 14 | Casa Noble Crystal | 78 | $39.99 |
| 15 | Corralejo Reposado | 75 | $24.99 |
| 16 | Herradura Añejo | 73 | $54.99 |
| 17 | Don Julio Añejo 70th Anniv. | 70 | $64.99 |
| 18 | Casamigos Tequila Blanco | 64 | $39.99 |
| 18 | Herradura Seleccion Suprema | 64 | $299.99 |
| 20 | Siete Leguas Blanco | 61 | $36.99 |
| 21 | Siete Leguas Reposado | 52 | $39.99 |
| 22 | Herradura Reposado | 51 | $42.99 |
| 23 | Cazadores Tequila Reposado | 49 | $26.99 |
| 24 | Tres Generaciones Añejo | 48 | $49.99 |
| 24 | Maestro Dobel Diamond | 48 | $39.99 |
| 26 | Gran Centenario Añejo | 47 | $29.99 |
| 27 | Espolon Reposado | 46 | $18.99 |
| 28 | Herradura Silver | 44 | $39.99 |
| 29 | El Tesoro Tequila Reposado | 43 | $46.99 |
| 30 | Siete Leguas Añejo | 42 | $44.99 |
| 31 | Don Julio Real | 40 | $349.99 |
| 32 | Tapatio Excelencia Extra Añejo | 39 | $159.99 |
| 32 | Milagro Select Barrel Reserve Reposado | 39 | $49.99 |
| 34 | Casamigos Tequila Añejo | 38 | $44.99 |
| 35 | Milagro Silver | 37 | $29.99 |
| 35 | Cabo Wabo Reposado | 37 | $39.99 |
| 35 | Olmeca Altos Plata | 37 | $19.99 |
| 35 | Tapatio Blanco | 37 | $32.99 1L |
| 39 | Avión Silver | 36 | $44.99 |
| 39 | Patron Añejo | 36 | $49.99 |
| 41 | Casa Noble Single Barrel Extra Añejo | 35 | $99.99 |
| 41 | Gran Patron Platinum | 35 | $169.99 |
| 41 | Don Pilar Extra Añejo | 35 | $139.99 |
| 44 | El Tesoro de Don Felipe Paradiso | 34 | $127.50 |
| 45 | Olmeca Altos Reposado | 33 | $19.99 |
| 46 | Corralejo Añejo | 32 | $29.99 |
| 46 | Casa Noble Single Barrel 6-year Extra Añejo | 32 | $129.99 |

Figure 1A

| Position | Tequila Name | Likes | Price |
|---|---|---|---|
| 48 | Espolon Blanco | 31 | $27.99 |
| 48 | Chamucos Reposado | 31 | $49.99 |
| 48 | t1 Añejo Estellar | 31 | $55.99 |
| 48 | Jose Cuervo Tradicional Reposado | 31 | |
| 48 | Casa Noble Single Barrel Reposado | 31 | $75 |
| 53 | El Tesoro Tequila Añejo | 30 | $49.99 |
| 53 | Arette Añejo | 30 | $34.99 |
| 53 | Gran Patron Burdeos | 30 | $398.98 |
| 56 | Patron Reposado | 29 | $46.99 |
| 56 | Kah Anejo | 29 | $57.99 |
| 58 | Don Pilar Añejo | 28 | $39.99 |
| 58 | Ocho Tequila Reposado | 28 | $49.99 |
| 58 | ArteNom Seleccion de 1146 Añejo | 28 | $56.99 |
| 58 | Ocho Tequila Plata | 28 | $42 |
| 62 | Tapatio Reposado | 27 | $37.99 1L |
| 62 | Milagro Select Barrel Reserve Silver | 27 | $44.99 |
| 62 | Chinaco Añejo | 27 | $54.99 |
| 65 | El Tesoro Tequila Platinum | 26 | |
| 65 | Milagro Reposado | 26 | $26.99 |
| 65 | Tres Agaves Reposado | 26 | $27.99 |
| 65 | Grand Mayan Extra Añejo (5 yr) | 26 | $75.99 |
| 65 | Arette Reposado | 25 | $26.99 |
| 65 | Tapatio Añejo | 25 | $41.99 1L |
| 65 | Kah Reposado | 25 | $49.99 |
| 65 | Milagro Select Barrel Reserve Añejo | 25 | $95.59 |
| 65 | Los Abuelos Blanco | 25 | |
| 74 | Tapatio Blanco 110 | 24 | $49.49 1L |
| 74 | 123 Organic Tequila Reposado | 24 | $47.99 |
| 74 | Camarena Reposado Tequila | 24 | |
| 74 | Arette Artesenal Blanco Suave | 24 | |
| 74 | Cabo Wabo Añejo | 24 | $49.99 |
| 74 | Tres Agaves Añejo | 24 | $29.99 |
| 74 | Tres Generaciones Reposado | 24 | $34.99 |
| 81 | Clase Azul Plata | 23 | $62.99 |
| 81 | El Tesoro de Don Felipe 70th Anniv | 23 | $199.99 |
| 81 | Partida Añejo | 23 | $49.99 |
| 81 | Gran Patron Piedra Extra Añejo | 23 | $299 |
| 81 | Gran Dovejo Blanco | 23 | $44.99 |
| 81 | 1800 Reposado | 23 | $49.99 1.75L |
| 81 | Corzo Añejo Tequila | 23 | $49.99 |
| 81 | Cazadores Tequila Añejo | 23 | $39.99 |
| 81 | Ocho Tequila Plata - El Puertecito 2011 | 23 | |
| 90 | Los Abuelos Añejo | 22 | |
| 90 | Ocho Tequila Añejo | 22 | $65.99 |
| 90 | San Matias Gran Reserva | 22 | $46.99 |
| 90 | Corzo Reposado Tequila | 22 | $46.99 |
| 90 | El Jimador Blanco Tequila | 22 | $21.99 |

Figure 1B

| Position | Tequila Name | Likes | Price |
|---|---|---|---|
| 90 | Partida Blanco | 22 | $39.99 |
| 90 | Partida Reposado | 22 | $46.99 |
| 90 | 123 Organic Tequila Añejo | 22 | $59.99 |
| 90 | Arette Blanco | 22 | $19.99 |
| 99 | Gran Dovejo Reposado | 21 | $49.99 |
| 99 | Ocho Tequila Plata - El Refugio 2012 | 21 | |
| 99 | Cava de Oro Extra Añejo | 21 | $89.99 |
| 99 | Corzo Silver Tequila | 21 | $45.99 |
| 99 | El Tesoro de Don Felipe 75th Anniv | 21 | $199.99 |
| 99 | D'Antaño | 21 | $249.99 |
| 99 | El Jimador Reposado Tequila | 21 | $23.99 |
| 99 | Los Abuelos Reposado | 21 | |
| 100 | 123 Organic Tequila Blanco | 20 | $42.99 |
| 100 | Ocho Tequila Extra Añejo | 20 | $139.89 |
| 100 | Gran Centenario Reposado | 20 | $29.99 |
| 100 | Dulce Vida Añejo | 20 | $52.99 |

Figure 1C

METHODS TO IMPROVE BEVERAGE QUALITY

CROSS-REFERENCE TO RELATED APPLICATIONS

This application claims priority to U.S. Provisional Application No. 62/917,188 filed 26 Nov. 2018, the contents of which are incorporated herein by reference in their entirety.

TECHNICAL FIELD

The invention is directed to improvements in compositions that comprise inhibitors of monoamine oxidase A (MAO A) and monoamine oxidase B (MAO B) that are found in distilled spirits derived from agave by adjustment of the ratios thereof. Also included are improved additional agents to the compositions.

BACKGROUND ART

U.S. Pat. 10,195,163, incorporated herein by reference, describes the production of compositions containing significant concentrations of inhibitors of MAO A and MAO B from tequilas and from pulque. Reverse osmosis and spinning cone column technologies are described as techniques for removing alcohol while preserving the activity of these inhibitors, as these inhibitors are volatile and may be formed during fermentation and distillation of tequila and fermentation of pulque. It is not at present known whether these represent single MAO inhibitors or more than one, so singular and plural are used herein interchangeably.

U.S. Patent Application No. 2018/0296629 published 18 Oct. 2018 describes improved methods to remove alcohol from the distillates. The contents of this document are incorporated herein by reference, but briefly, methods that include reverse osmosis and low pressure evaporation to provide retentates with significant concentrations of these inhibitors are described. In addition, details of assay methods for monoamine oxidase activity (and therefore inhibition thereof) and for ethanol content are provided.

There appears to be no recognition that the ratio of inhibitors derived ultimately from agave of monoamine oxidase B to those of monoamine oxidase A is of significance, or that the concentration of MAO B inhibitor is especially important. In both cases, these inhibitors are reversible as demonstrated in the foregoing '629 publication.

DISCLOSURE OF THE INVENTION

In one aspect, the present invention is based on the recognition that the ratio of the inhibitor contained in agave-derived distillates for inhibition of MAO B as compared to inhibition of MAO A is significant, as is the concentration of the MAO B inhibitor per se. It is now understood that the quality of either the fermented agave distillate itself used as a beverage or of a derivative relatively nonalcoholic form thereof is at least in part determined by the ratio of inhibitors of monoamine oxidases A and B and/or the concentration of MAO B inhibitor.

Thus, the invention is directed to a method to improve the quality of a beverage which is tequila or mezcal or a drink with reduced alcohol content derived therefrom which method comprises altering the ratio of inhibitor of MAO B to inhibitor of MAO A contained therein to increase this ratio in favor of B and/or increasing the concentration of the MAO B inhibitor. Beverages that are thus obtained and methods to treat depression and Parkinson's disease and to enhance cognition by providing the reduced alcohol forms of these beverages are also part of the invention.

In another aspect, the invention is directed to important additional synergistic and/or preservative components that may be added to the reduced alcohol composition obtained from the distillates, including those with the altered ratio of inhibitors as noted above.

BRIEF DESCRIPTION OF THE DRAWINGS

FIG. 1A-1C shows the results of tests to evaluate the perceived quality of Don Julio tequilas.

MODES OF CARRYING OUT THE INVENTION

Figure 2:
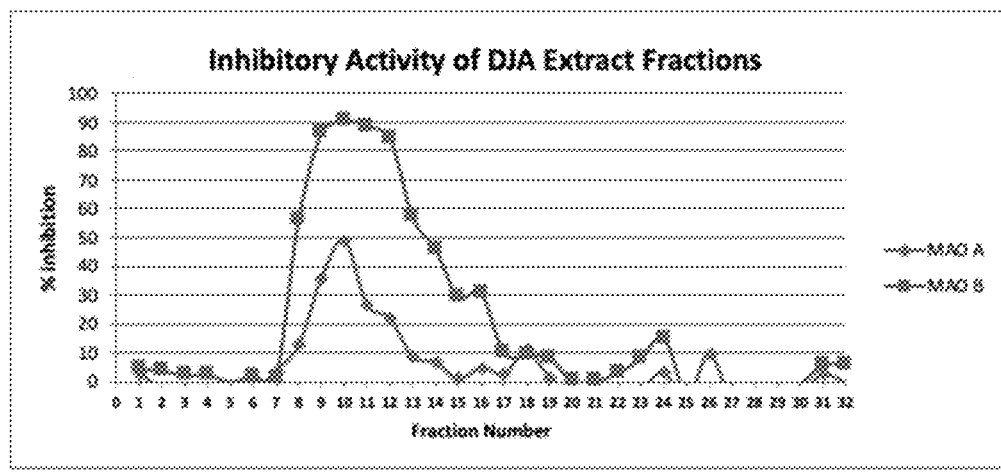
FIG. 2 shows the resolution of both MAO A and MAO B inhibitory activity on a silica gel column.

With respect to the first aspect of the invention, the quality of a beverage which is tequila or mezcal or a drink with reduced alcohol content derived therefrom is improved by altering the ratio of inhibitor of MAO B to inhibitor of MAO A contained therein to increase this ratio in favor of B and/or simply increasing the concentration of the MAO B inhibitor.

The drink with reduced alcohol will have low enough values of alcohol by volume (ABV) to be useful as a food supplement or as a medicament that can be used, for example, for treatment of depression or Parkinson's or to enhance cognition. Typical values of ABV are 2% or less, or 1.5% or less, or 1% or less, or 0.5% or less.

One method of achieving both low ABV and alteration of inhibitor ratio comprises isolation of MAO A and MAO B inhibitors from tequila while reducing the alcohol concentration to produce a low alcohol beverage with mood elevating properties using reverse osmosis with membranes that substantially retain NaCl in the retentate. Tequila is a preferred starting material for this membrane-based method since it has high levels of MAO inhibitors and as a distillate it is without particulates that could affect membrane performance. The membrane based method using a 90%-99% NaCl rejection membrane maintains or increases the concentration of MAO B inhibitor in the retentate, while more of the MAO A inhibitors pass across the RO membrane in the permeate with ethanol and water. This is in comparison to the use of a nanofiltration membrane which is permeable to NaCl as such membranes have molecular weight cut-off values of 300 Daltons or greater. (Nanofiltration membranes are typically used in water softeners). The permeate may be collected or directed into another RO system fitted with a nanofiltration membrane to separate MAO A inhibitors from ethanol, wherein at least some MAO A inhibitor remains in the concentrate while water and ethanol are in the permeate.

Another method is, of course, simply to add inhibitor to MAO B that has been enriched or purified from an additional sample of the tequila, mezcal or reduced alcohol form. The sample may be of the same beverage or a different member of the class of beverages. Methods to separate or enrich individual compounds from complex mixtures are known in the art, including various chromatographic methods such as HPLC.

It is understood that MAO inhibitors are used to treat depression, inhibitors of MAO B are also used to treat Parkinson's disease. Increased MAO B activity is associated with aging and cognitive decline in humans. MAO B catalyzes the metabolism of phenylethylamine (2-phenylethylamine, PEA), a neurotransmitter classified as a trace amine with effects similar to amphetamine that is believed to increase the concentration of serotonin and dopamine in the synaptic cleft by inhibiting re-uptake of those neurotransmitters. Trace amines are present in significantly lower concentration than other functional amine neurotransmitters, but PEA has a potent effect by its mechanism of action that involves binding to a G protein coupled receptor of the type that is also activated by amphetamine. Metabolic breakdown of PEA is thus a depressant and MAO B metabolism of amines generates hydrogen peroxide as a byproduct, which affects cognition.

It is understood that MAO B inhibition increases levels of phenylethylamine, which increases levels of serotonin and dopamine for positive experiential effects. Thus, enhanced levels of MAO B inhibitor provide the ability to improve cognition.

In another aspect, the invention relates to providing helpful synergistic and/or preservative agents to the agave distillate derived non-alcoholic beverage either per se, or to the improved beverage with an enhanced MAO B inhibitor to MAO A inhibitor of the invention. For example, adding PEA as a synergistic agent is of benefit. It is known that oral administration of PEA is ineffective due to the high activity of MAOs in the gut and plasma compartment, which rapidly metabolizes PEA, but the MAO B inhibitor containing beverage increases the level of absorption of PEA and other biogenic amines by inhibiting MAOs normally encountered along absorption pathways. In addition, caffeine is used in combination with PEA.

Additional preservative ingredients include components that stabilize the drink and incidentally provide additional nutritional benefits. These include proteins, any protein provides stability to the MAO inhibitor containing drink. The inhibitors adsorb to the proteins and are prevented from precipitating out of solution as the ethanol concentration decreases. Preservatives such as propylene glycol may also be added. In the US, the Food and Drug Administration allow alcoholic beverages to contain up to 5% propylene glycol and European rules allow 3 grams per kg in flavorings, and 0.1% in beverages.

Other preservative agents include sodium benzoate, sulphur dioxide, sorbic acid and its salts or benzoic acid to inhibit any bacterial growth. The maximum permitted level for benzoic acid in soft drinks is 150 mg/l and sorbic acid is 300 mg/l when used singly, or 250 mg/l when used in combination with a benzoate.

Thus, in one illustrative embodiment ethanol is removed to a desired level with simultaneous removal of MAO A inhibitors and retention of MAO B inhibitors resulting in an effective concentration and desired ratio of inhibitors MAO A/MAO B to produce the desired experiential effect. Inhibitor of MAO B previously obtained from tequila or the reduced alcohol derivative thereof can be added directly, for example. The ratio of inhibitors may be adjusted according to personal preferences.

In some embodiments, a 12 oz dose of the reduced alcohol beverage (with or without MAO B inhibitor adjustment) contains 100 to 300 mg phenylethylamine citrate, 100 to 300 mg phenylethylamine hydrochloride and 15 to 200 mg caffeine. Protein from milk such as, β-lactoglobulin, α-lactalbumin, bovine serum albumin, whey and caseins are added to the drink at a concentration of 10 to 30 grams per 12 oz volume. The MAO inhibitors are adsorbed to the proteins and therefore the proteins provide an increase in stability to the beverage preventing precipitation in the absence of ethanol. The solvent effect of alcohol may also be replaced by the addition of propylene glycol in some formulations. In addition, electrolytes or vitamin B complex are optionally included.

In summary, the experiential quality of tequila or mezcal can be improved according to the invention by adjusting the ratio of inhibitors of MAO B and MAO A in favor of B or by simply increasing the concentration of B inhibitor. The quality as a medicament of the reduced alcohol drink derived therefrom can also be improved by these methods. The reduced alcohol drink derived from tequila or mezcal, whether or not altered by adjusting the inhibitors, can also be improved as a medicament by synergistic and/or preservative agents.

The following examples are to illustrate, but not to limit the invention.

Example 1

Alteration of Inhibitor Ratio

Some known MAO inhibitors cross-react with both MAO A and B, however, the inhibitors present in tequila are specific inhibitors for either form of monoamine oxidase. This is seen in the activity assay results comparing Don Julio Anejo (DJA) and Casa Dragones (CD) brands. CD shows a ratio of B/A inhibitors of 6, while the ratio in DJA is 3.4.

Table 1 shows inhibitory activity in DJA and CD tequilas. These percentages are taken in the tequila per se and do not reflect the levels obtained below with a nanofiltration membrane to remove the alcohol.

TABLE 1

|  | % Inhibition MAO A | % Inhibition MAO B |
|---|---|---|
| Casa Dragones Blanco | 9 | 54 |
| Don Julio Anejo | 21 | 71 |

Don Julio Anejo tequila (DJA) 5 L was diluted to 40 L and concentrated back to 5 L (batch mode) in a reverse osmosis (RO) Alfa Laval M20 RO processor, followed by further recirculating with the volume maintained at 5 L (diafiltration mode) until the ethanol concentration was lowered to ~1.3% ABV. The RO processor was equipped with a 90% NaCl rejection membrane (RO90).

For comparison, DJA was processed under the same conditions except with a 95% NaCl rejection membrane, a 99% NaCl rejection membrane and a nanofiltration (NF) membrane.

Table 2 shows MAO inhibitory activity in the resulting RO concentrates from the four membranes. The 90-99% NaCl rejection membranes effectively maintain most of the MAO B inhibitor concentration but somewhat reduce the MAO A inhibitor concentration providing an improved final product through retention of MAO B inhibitors. The nanofiltration membrane (NF) reflects a standard of comparison for alcohol removal per se since it is permeable to NaCl.

TABLE 2

| Membrane | MAO A % inhibition | MAO B % inhibition | B:A inhibition |
|---|---|---|---|
| 90% NaCl Rejection RO | 11 | 43 | 4 |
| 95% NaCl | 20 | 40 | 2 |

TABLE 2-continued

| Membrane | MAO A % inhibition | MAO B % inhibition | B:A inhibition |
|---|---|---|---|
| Rejection RO 99% NaCl | 5 | 30 | 6 |
| Rejection RO NF | 17 | 25 | 1.2 |

Example 2

Effect of MAO B Inhibitor Concentration

There are ~139 tequila distilleries in Mexico producing over 1000 different retail brands, each producer is identified in the Norma Official Mexicana (NOM) database by a registration number that appears on each bottle produced. There is a range of MAO A and B inhibitor activities across the NOM database of distilleries, but consistent inhibitor concentrations are seen in MAO activity assays run on sample tequilas from each distiller. FIG. 1 shows the quality rankings of tequila brands as obtained from the web site: tastetequila.com/2015/100-favorite-tequila-brands-according-to-hardcore-fans/. Table 3 shows the Don Julio brands with MAO inhibitory activity and the "likes" as they are rated.

TABLE 3

| Brand | % Inhibition MAO A | % Inhibition MAO B | Likes |
|---|---|---|---|
| Don Julio 1942 | 18 | 35 | 290 |
| Don Julio Añejo | 10 | 26 | 141 |
| Don Julio Reposado | 18 | 22 | 113 |
| Don Julio Blanco | 9 | 8 | 106 |
| Don Julio 70th | 12 | 6 | 70 |

Interestingly, in the case of the Don Julio $70^{th}$, which is the Don Julio Añejo after an additional distillation (and filtration), there is a significant loss of MAO B inhibitory activity from 26% down to 6% as well as a decreased number of likes from 141 to 70. The additional processing spoils the añejo tequila's "likability" by decreasing MAO B inhibitors. DJ1942 came out as number one of the top twenty in these ratings. It is noted there is no specific correlation with cost.

Example 3

Separation of MAO A and MAO B Inhibitors

Solvent extracts of two tequilas were made as follows: Tequila (300 ml) was diluted to 600 ml with deionized water and extracted with dichloromethane (3×125 ml). The extracts were combined and passed over a column of anhydrous sodium sulfate. Solvent was removed by evaporation in a Kuderna Danish apparatus warmed over a water bath at 70° C. Don Julio Anejo (DJA) and Casa Dragones Blanco (CD), were partially purified by silica gel chromatography run with 95% dichloromethane/5% methanol. Fractions (300 µL) were collected and each was assayed for MAO A and MAO B inhibitory activity. The fractions with inhibitory activity were further fractionated by HPLC and analyzed by mass spectrometry. FIG. 2 shows MAO A and MAO B inhibitory activity of DJA silica gel column fractions which contain the molecular weights: 194, 281, 283, 315, 386, 472, 473, 498, 506, 512, 527, 566, 586.

Figure 3:
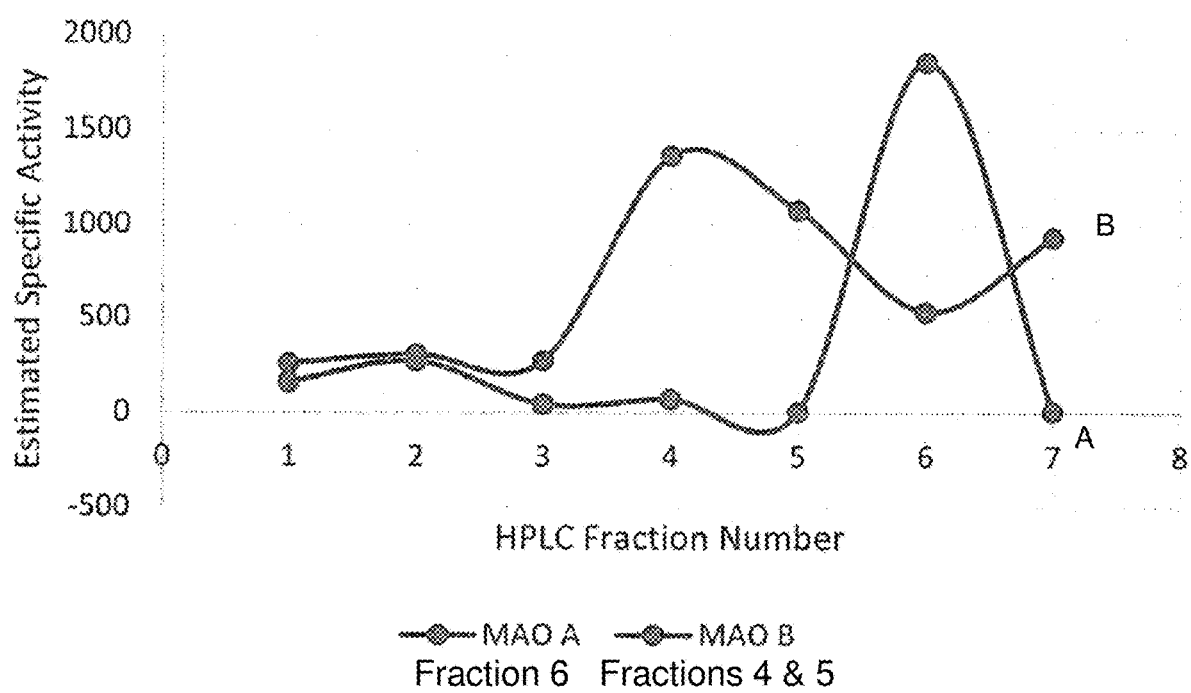
FIG. 3 shows the results of HPLC separation of inhibitors of MAO A and MAO B.

Further separation of the inhibitors was accomplished using HPLC as shown in FIG. 3. The molecular weights of the B fractions are 292 and 932 g/mole and of the A fractions 436 and 399 g/mole.

The invention claimed is:

1. A method to improve the quality of a beverage which is tequila or mezcal or a drink with alcohol by volume (ABV) of 2% or less produced therefrom, which method comprises altering the ratio of inhibitors of monoamine oxidases A and B (MAO A and MAO B) contained therein to increase the ratio of inhibitor of MAO B to that of MAO A, wherein the altering comprises subjecting the beverage to reverse osmosis with a 90%-99% NaCl rejection membrane.

2. The method of claim 1, wherein the improved quality is the experiential perception of a person consuming the improved beverage.

3. The method of claim 1, wherein the beverage is the drink with ABV of 2% or less, and the improved quality is of cognitive enhancement exhibited by a person consuming the improved beverage.

4. The method of claim 1, wherein the altering further comprises adding inhibitor of MAO B isolated from tequila or mezcal or a drink with ABV of 2% or less produced therefrom to the beverage.

5. The method of claim 1, wherein the altering comprises subjecting the beverage to reverse osmosis with:
   a 90% NaCl rejection membrane to increase the concentration of inhibitor of MAO B;
   a 95% NaCl rejection membrane to increase the concentration of inhibitor of MAO B; or
   a 99% NaCl rejection membrane to decrease the concentration of inhibitor of MAO A.

* * * * *